United States Patent [19]
Migliorini

[11] Patent Number: 5,391,890
[45] Date of Patent: Feb. 21, 1995

[54] METHOD OF SENSING VARIATIONS IN A CONSISTENCY OF A FABRIC AND AN APPARATUS FOR CARRYING OUT SUCH METHOD

[75] Inventor: Pier L. Migliorini, Terranuova Bracciolini, Italy

[73] Assignee: Solis S.R.L., Florence, Italy

[21] Appl. No.: 43,829

[22] Filed: Apr. 6, 1993

[30] Foreign Application Priority Data

Apr. 10, 1992 [IT] Italy .................................... FI92A88

[51] Int. Cl.⁶ ............................................. G01N 21/32
[52] U.S. Cl. ............................. 250/559; 250/214 RC; 250/563; 356/430
[58] Field of Search ............................. 250/559–562, 250/571, 572, 214 RC, 563; 356/237, 238, 239, 429, 430

[56] References Cited

U.S. PATENT DOCUMENTS

| | | |
|---|---|---|
| 3,560,751 | 2/1971 | Buettner .................. 250/214 RC |
| 3,584,963 | 6/1971 | Wisner ........................ 250/563 |
| 3,835,332 | 9/1974 | Bridges ....................... 250/563 |
| 3,859,537 | 1/1975 | Wolf ............................ 250/563 |
| 3,866,054 | 2/1975 | Wolf ............................ 250/563 |
| 3,918,815 | 11/1975 | Gadbois ..................... 250/559 |
| 3,942,898 | 3/1976 | Anderson .................. 250/559 |
| 4,011,457 | 3/1977 | Wolf ...................... 250/214 RC |
| 4,054,377 | 10/1977 | Gibson ....................... 250/563 |
| 4,253,113 | 2/1981 | Decavel et al. ............ 250/563 |
| 4,349,880 | 9/1982 | Southgate et al. ........ 250/563 |

*Primary Examiner*—David C. Nelms
*Assistant Examiner*—Stephone B. Allen
*Attorney, Agent, or Firm*—McGlew and Tuttle

[57] ABSTRACT

The apparatus has an optical reflecting sensor, an operational amplifier buffer with the electrical input connected to the output of the optical sensor, structure for averaging and delating a signal picked up at the output of the sensor, structure for the differential amplification of the signals on output respectively from the buffer and structure for comparing the signal outputting from the means with a known predetermined signal.

4 Claims, 3 Drawing Sheets

METHOD OF SENSING VARIATIONS IN A CONSISTENCY OF A FABRIC AND AN APPARATUS FOR CARRYING OUT SUCH METHOD

FIELD OF THE INVENTION

The present invention refers to a method of sensing the varying of consistency of a fabric, and an apparatus for carrying out the method.

BACKGROUND OF THE INVENTION

It is known that in the textile industry the problem of sensing fabrics discontinuity due, for example, to a seam or superimposition of fabrics of different characteristics, or even to variation of consistency of a same fabric, is of primary concern.

In particular, the problem is mostly present in the production of pantyhose and finishing of stockings. It is known, in fact, that a particularly important step of the process for making a pantyhose article is the one concerning the automatic positioning of the stockings before cutting them lengthwise. The positioning is made possible by detecting the garter line of each of the two stockings. The garter line being generated by the variation of fabric consistency in correspondence of the line of junction between the bodice and the stocking leg.

The known methods and devices for the detection of the garter line make use of means for driving the stocking on corresponding supports in order to temporarily stretch the fabric, that is, make it wrinkle-free, and allow a suitable optical sensor to sense the line.

The drawbacks deriving from the use of these methods and devices lie essentially in that they imply the need of stretching the fabric on the support means and, as these have a length less than the distance between the garter line and the elastic hem of the stocking, of firstly carrying the garter line over the support means and, after the detection thereof, bringing it back to a predetermined position outside and beyond the support means. This driving operation is time consuming also because of the sensor sensitivity.

SUMMARY AND OBJECTS OF THE INVENTION

The present invention has the object to eliminate these drawbacks.

This result has been achieved, according to the invention, by adopting an operative method which consists of:
  moving the fabric to be treated relative to a fixed optical reflecting sensor provided for sensing the variation of the fabric consistency;
  picking up the signal on output from the sensor and sending, in parallel, the thus picked up signal to an operational amplifier buffer and to means for averaging and delaying the signal;
  sending the signals on output respectively from the buffer and from the means for averaging and delaying the signal picked-up from the optical means to a differential amplifier;
  sending the output signal from the differential amplifier to the input of a comparator which compares this signal with a known and predetermined signal;
  sending the output signal from the comparator to the operative means for the subsequent treatment of the fabric when the output signal from the amplifier has an intensity exceeding a predetermined value.

To implement the method an apparatus is used, with an optical sensor for detecting the line of fabric discontinuity, characterized in that it comprises:
  an operational amplifier buffer with the input electrically connected to the output of the optical sensor;
  means for averaging and delating the output signal from the optical sensor;
  means for the differential amplification of signals outputting from the buffer and from the means for averaging and delating the output signal of the optical sensor;
  means for comparing the signal outputting from the differential amplification means with a known and predetermined signal;
  means for utilizing the signal outputting from the comparing means.

The advantages deriving from the present invention lie essentially in that it is possible to sense the discontinuity, that is, a line of demarcation of the consistency of a fabric without the need of undergoing the latter to a particular draw, so that a significant simplification in the construction and running of the apparatus is obtained together with a high reliability thereof; that it is possible to detect even minimum variations of consistency; that the time for sensing a discontinuity on the fabric results greatly reduced owing to the elimination of operating steps related to the stretching of the fabric before this is placed in correspondence of the detection sensor.

BRIEF DESCRIPTION OF THE DRAWINGS

These and other advantages and characteristics of the invention will be best understood by anyone skilled in the art from a reading of the following description in conjunction with the attached drawings given as a practical exemplification of the invention, but not to be considered in a limitative sense, wherein.

DETAILED DESCRIPTION OF THE PREFERRED EMBODIMENT

Figure 1:
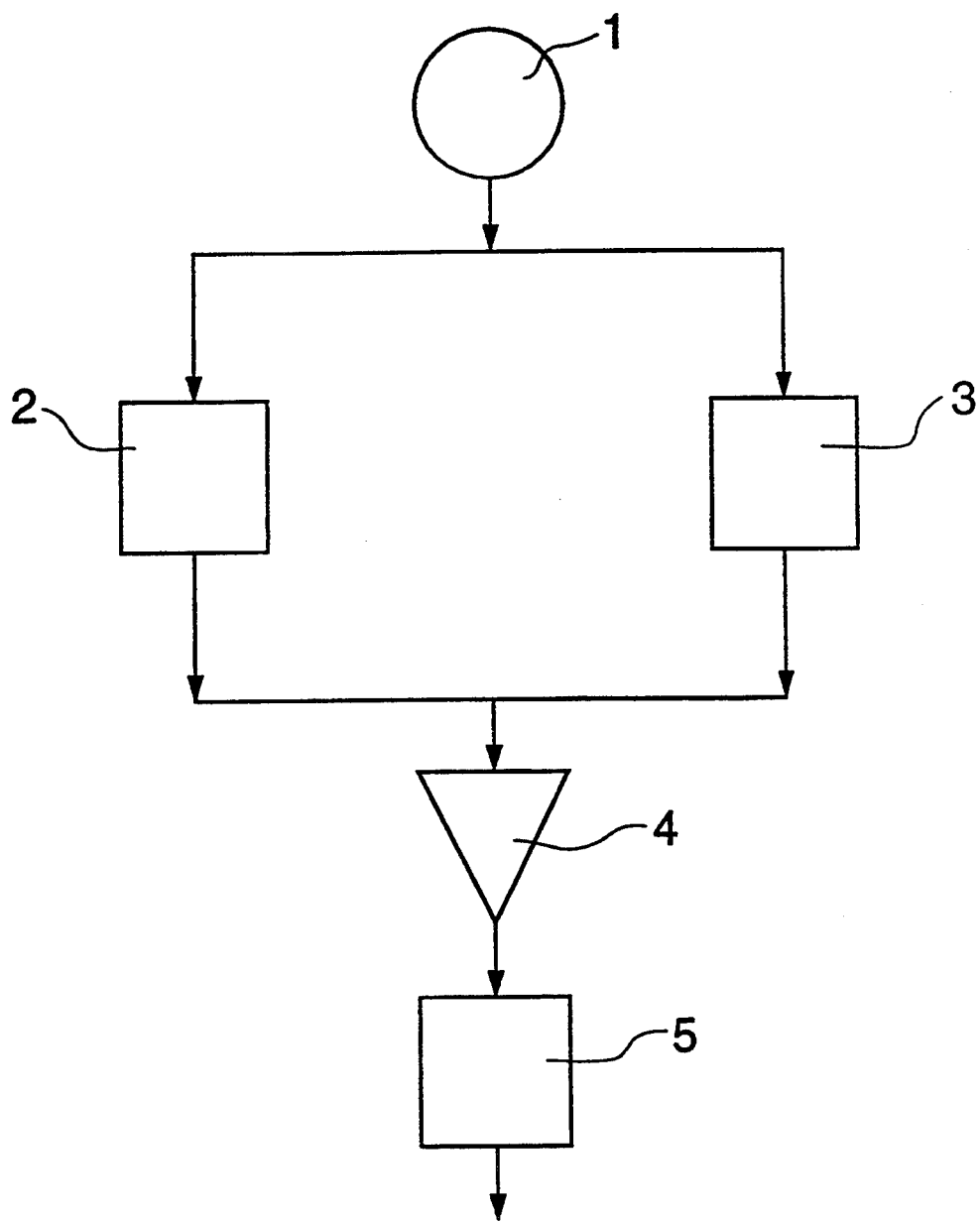
FIG. 1 shows the block diagram of an apparatus according to the invention.

Reduced to its basic structure, reference being made to the accompanying drawings, the method for sensing the variation of consistency of a fabric, according to the invention, includes, in sequence, the following operating steps:
  moving the fabric to be treated relative to a fixed optical reflecting sensor (1) provided for sensing the variation of the fabric consistency;
  picking up the signal on output from the optical sensor (1) and sending, in parallel, the thus picked up signal to an operational amplifier buffer (3) and to means (2) for averaging and delaying the signal;
  sending the signals on output respectively from the buffer (3) and from the averaging and delaying means (2) to a differential amplifier;
  sending the output signal from the differential amplifier (4) to the input of a comparator (5) which compares this signal with a known and predetermined signal;

sending the output signal from the comparator (5) to the operative means for the subsequent treatment of the fabric when the output signal from the amplifier has an intensity exceeding a predetermined value.

Advantageously, provision is made that the known and predetermined signal be variable at will, to meet the user's requirements.

As for the apparatus for carrying out the method according to the invention, it is provided with:
- a fixed optical reflecting sensor (1) for sensing the variation of a fabric consistency, such as the garter line of a stocking for ladies;
- an operational amplifier buffer (3) with the input electrically connected to the output of the optical sensor (1);
- means (2) for averaging and delaying the output signal of the optical means (1);
- means (4) for the differential amplification of the signal outputting from the buffer (3) and from the means (2) for averaging and delaying the output signal of the optical sensor (1);
- means (5) for comparing the output signal from the differential amplification means (4) with a known and predetermined signal;
- means (not shown for sake of clarity in the figures) for utilizing the output signal from the comparing means (5) when the output signal from differential amplification means (4) has an intensity exceeding a predetermined value, in order, for example, to stop the movement of the stocking with respect to the sensor.

Figure 2:
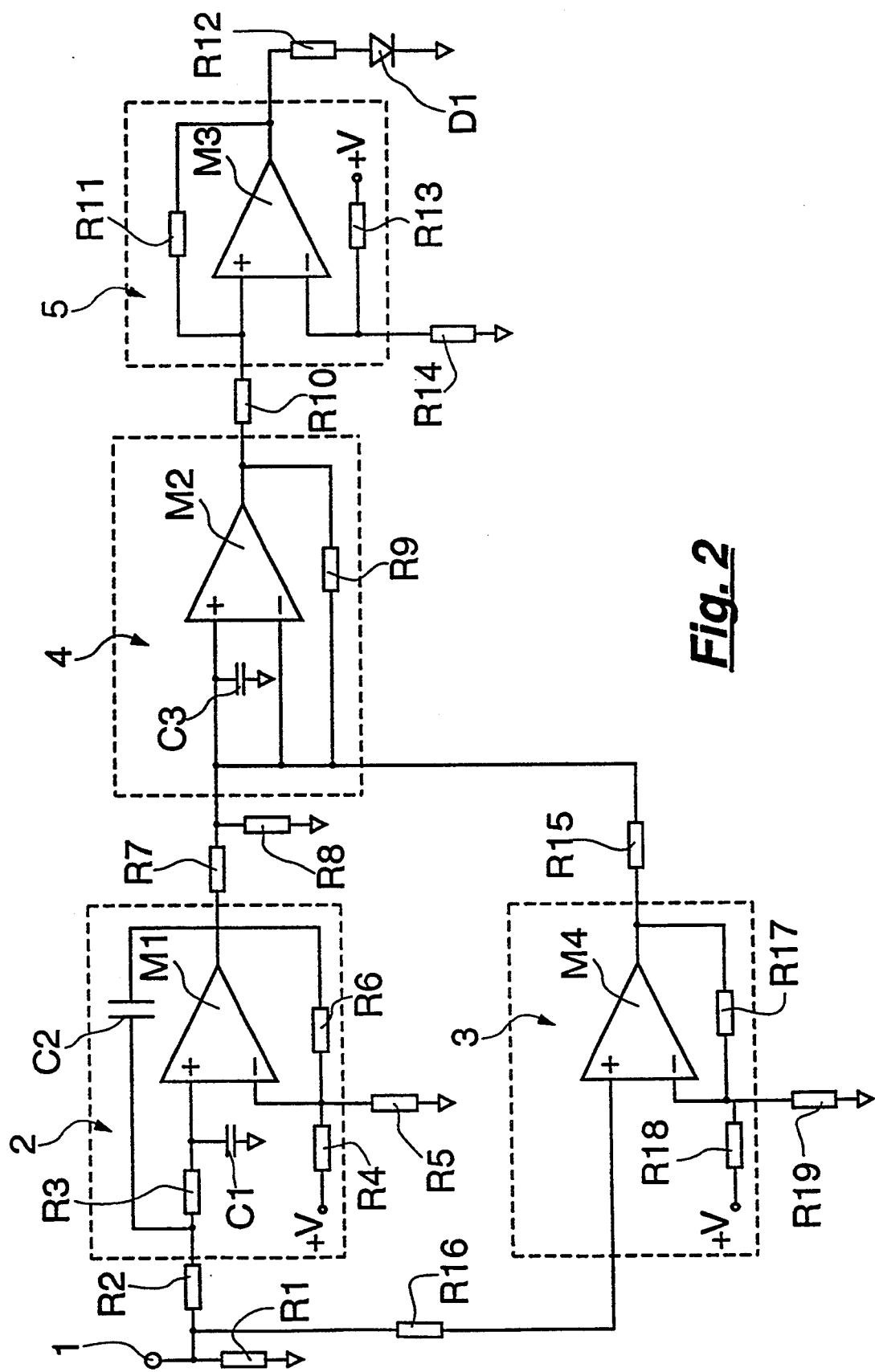
FIG. 2 shows the wiring diagram relating to a preferred embodiment of an apparatus according to the invention.
Figure 3:
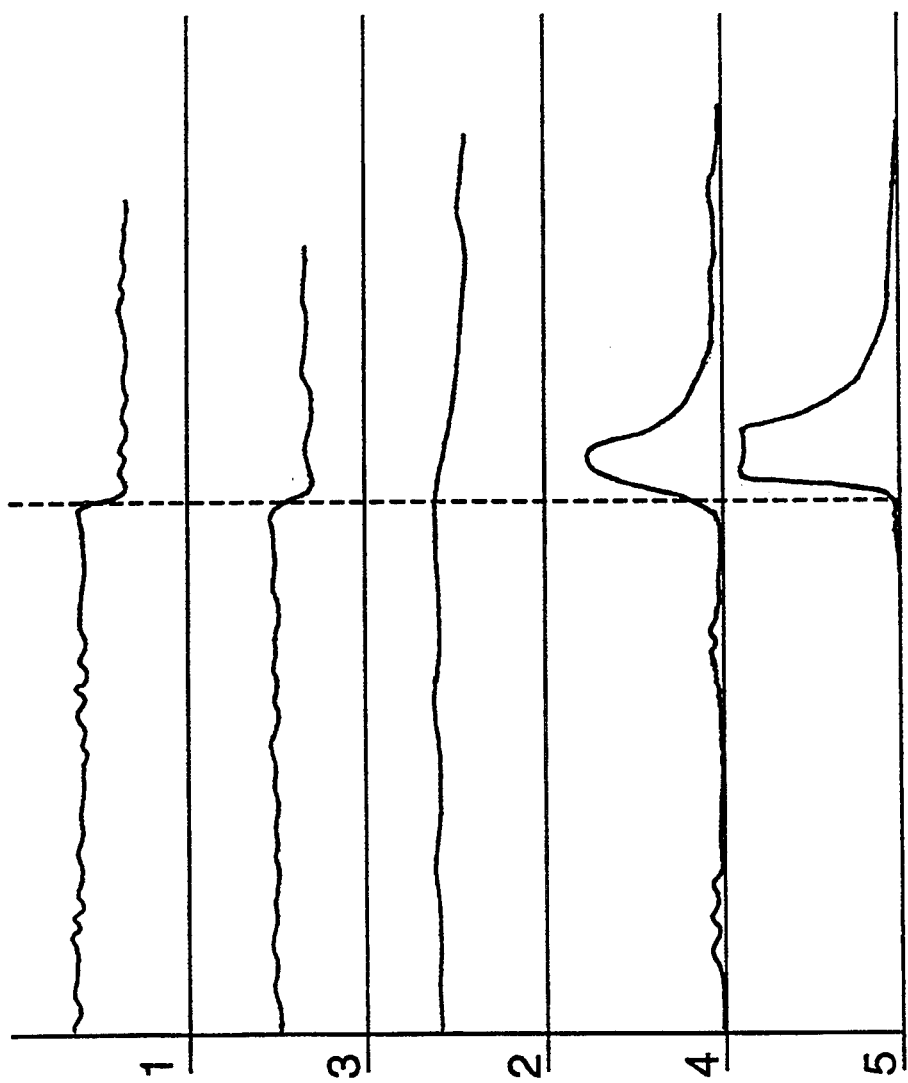
FIG. 3 shows the graphs or waveforms of the output signals from the operative elements of FIG. 2.

More particularly, and with reference to FIG. 2 of the attached drawings, a resistence (R1) is provided shunt-connected on the point of junction of the output of the optical sensor (1) with the input of buffer (3).

The means (2) for averaging and delaying the signal outputting from the optical sensor (1) are electrically connected, via a series resistance (R2), to the output of the optical sensor (1) and comprise a low-pass filter (M1) to allow only the transit of signals having known and predetermined frequencies, with a capacitor (C2) in parallel between the output of the resistance (R2) and the output of same means (2), with a resistance (R3) downstream of the point of connection of the capacitor (C2) to the output of the resistance (R2), which resistance (R3) is connected in series to the resistance (R2), with a capacitor (C1) shunt-connected on the output of resistance (R3), with a resistance (R4) connected, by one end, to a 24-volt source and, by the other, to the negative input of the means (2), with a resistance (R6) in series between the output of the resistance (R4) and the output of the capacitor (C2) and with a resistance (R5) shunt connected on the point of junction of the resistance (R4) to the resistance (R6).

The operational amplifier buffer (3) is connected to the output of the optical sensor (1) via a series resistance (R16) and is provided with a resistance (R18) having a 24-volt tension applied to one end thereof and connected in series to a resistance (R17) derived between the input and the output of the buffer (3) and to a resistance (R19) shunt connected on the point of junction of the resistance (R17) with the resistance (R18).

The differential amplification means (4) comprise a differential amplifier (M2) having its positive input terminal connected, via a resistance (R7), with the output of the means (2) for averaging and delating the signal from the photocell (1) and further connected, via a resistance (R15), with the output of buffer (3).

Advantageously, the positive and negative inputs of the differential amplifier (M2) are connected through a capacitor (C3).

A resistance (R9) is connected on one end to the output of the resistance (R7) and on the other, to the output of the amplifier (M2), while a resistance (R8) is shunt-connected on the point of junction of the resistance (R7) with the positive input terminal of the amplifier (M2).

The negative input of the comparator (M3) is connected with one end of a resistance (R14): connected to the point of junction of the negative input of the comparator (M3) with the resistance (R14), is one end of a resistance (R13), the other end of which being connected to the positive pole of a 24-volt tension source. Connected in series to the output of the comparator (5) is a resistance (R12) with a cascade diode (D1).

Given below, by way of example and with reference to a preferred embodiment of the invention, are the characteristics relevant to the wiring elements of FIG. 2:

R1=kn
R2, R3, R4, R5, R6, R7=100 kn
R8, R9=470 kn
R10=100 kn
R11=1 Mn
R12=2.2 kn
R13=100 kn
R14=47 kn
R15, R16, R17, R18, R9=100 kn
C=1 uF
C2=47 kpF
C3=10 kpF
M1, M2, M3, M4: type LM324
D1: type 1N4148

The operation is as follows.

The fabric is driven relative to the optical sensor (1) which generates an electrical signal fed in parallel to the low-pass filter (2) and buffer (3). The signal feeding the low-pass filter is thus averaged, while the one fed to the buffer (3) is retransmitted unchanged. The output signal from the low-pass filter (2) and buffer (3) are sent to the differential amplifier (4) which provides for amplifying the difference between the averaged signal and the instantaneous signal which is transmitted from the buffer (3). The output signal from the differential amplifier is then delivered to the comparator (5) which compares the input signal with a reference one being known and predetermined. If an inequality is found between the signal outputting from the amplifier and the said known reference signal, the comparator activates the corresponding means for the fabric treatment. The inequality being found when the optical sensor (1) detects a difference of consistency or colour of the fabric and, thereby, producing an electrical signal having intensity and frequence corresponding to the intensity and frequency of the signal for which the comparator (5) is set.

Practically, all the construction details may vary in any equivalent way as far as the shape, dimensions, elements disposition, nature of the used materials are concerned, without nevertheless departing from the scope of the adopted solution idea and, thereby, remaining within the limits of the protection granted to the present patent for industrial invention.

I claim:

1. A device for sensing variations in a consistency of a fabric, the device comprising:

optical reflecting sensor means for generating a signal proportional to the consistency of the fabric;

means for dividing said signal into a first part and a second part;

means for averaging and delaying said first part of said signal;

differential amplifying means for amplifying a difference between said second part of said signal and said first part of said signal from said means for averaging and delaying;

comparing means for comparing said amplified difference from said differential amplifier with a predetermined value and for generating an output signal when said amplified difference is greater than said predetermined value to indicate a variation in the consistency of the fabric;

a first resistor is connected between an output of said optical reflecting sensor means and ground;

a second resistor is connected between said output of said optical reflecting sensor means and an input of said means for averaging and delaying;

a third resistor is connected between said second resistor and a plus terminal of an operational amplifier of said means a plus terminal of an operational amplifier of said means for averaging and delaying;

a fourth resistor is connected between a voltage source and a minus terminal of said operational amplifier of said means for averaging and delaying;

a fifth resistor is connected between ground and said minus terminal of said operational amplifier of said means for averaging and delaying;

a sixth resistor is connected between said minus terminal and an output terminal of said operational amplifier of said means for averaging and delaying;

a seventh resistor is connected between said output terminal of said operational amplifier of said means for averaging and delaying and a plus terminal of an operational amplifier of said differential amplifier means;

an eighth resistor is connected between ground and said plus terminal of said operational amplifier of said differential amplifier means;

a ninth resistor is connected between said minus terminal and an output terminal of said operational amplifier of said differential amplifier means;

a tenth resistor is connected between said output terminal of said operational amplifier of said differential amplifier means and a plus terminal of an operational amplifier of said comparing means;

an eleventh resistor is connected between said plus terminal and an output terminal of said operational amplifier of said comparing means;

a twelfth resistor is connected at one end to said output terminal of said operational amplifier of said comparing means;

a thirteenth resistor is connected between a voltage source and a minus terminal of said operational amplifier of said comparing means;

a fourteenth resistor is connected between ground and said minus terminal of said operational amplifier of said comparing means;

an operational amplifier buffer receives said second part of said signal from said optical reflecting sensor;

a fifteenth resistor is connected between an output terminal of an operational amplifier of said operational amplifier buffer and said minus terminal of said operational amplifier of said differential amplifier means;

a sixteenth resistor is connected between said output of said optical reflecting sensor means and an input of said operational amplifier buffer;

an seventeenth resistor is connected between a minus terminal and said output terminal of said operational amplifier of said operational amplifier buffer;

an eighteenth resistor is connected between a voltage source and a minus terminal of said operational amplifier of said operational amplifier buffer;

a nineteenth resistor is connected between ground and said minus terminal of said operational amplifier of said operational amplifier buffer;

a first capacitor is connected between ground and said plus terminal of said operational amplifier of said means for averaging and delaying;

a second capacitor is connected between said input of said means for averaging and delaying and said output terminal of said operational amplifier of said means for averaging and delaying;

a third capacitor is connected between said plus terminal and said output terminal of said operational amplifier of said differential amplifier means.

2. A device in accordance with claim 1, wherein:
   said means for averaging and delaying includes a low pass filter.

3. A device in accordance with claim 1, wherein:
   said differential amplifying means includes a differential amplifier.

4. A device in accordance with claim 1, wherein:
   said comparing means includes a variable threshold comparator.

* * * * *